United States Patent
Bernstein

(10) Patent No.: US 9,545,419 B1
(45) Date of Patent: Jan. 17, 2017

(54) METHOD AND COMPOSITIONS FOR TREATING CHRONIC INFLAMMATORY DISORDERS

(71) Applicant: Joel E Bernstein, Highland Park, IL (US)

(72) Inventor: Joel E Bernstein, Highland Park, IL (US)

(73) Assignee: ELORAC INC, Vernon Hills, IL (US)

( * ) Notice: Subject to any disclaimer, the term of this patent is extended or adjusted under 35 U.S.C. 154(b) by 0 days.

(21) Appl. No.: 14/950,030

(22) Filed: Nov. 24, 2015

(51) Int. Cl.
*A01N 43/04* (2006.01)
*A61K 31/70* (2006.01)
*A61K 9/00* (2006.01)
*A61K 9/48* (2006.01)
*A61K 31/202* (2006.01)
*A61K 31/352* (2006.01)
*A61K 31/353* (2006.01)
*A61K 31/455* (2006.01)
*A61K 31/7084* (2006.01)
*A61K 31/12* (2006.01)

(52) U.S. Cl.
CPC ......... *A61K 31/7084* (2013.01); *A61K 9/0019* (2013.01); *A61K 9/0053* (2013.01); *A61K 9/48* (2013.01); *A61K 31/12* (2013.01); *A61K 31/202* (2013.01); *A61K 31/352* (2013.01); *A61K 31/353* (2013.01); *A61K 31/455* (2013.01)

(58) Field of Classification Search
None
See application file for complete search history.

(56) References Cited

FOREIGN PATENT DOCUMENTS

WO    WO 2015099842 A1 * 7/2015 ........... A23L 1/3002

OTHER PUBLICATIONS

Quercetin inhibits a large panel of kinases implicated in cancer cell biology, International Journal of Oncology, pub 2011, #38, pp. 833-843, Rainatou Boly et al.
Quercetin, a Flavonoid Phytoestrogen, Ameliorates Experimental Allergic Encephalomylitis by By Blocking IL-12 Signaling Through JAK-STAT Pathway in T Lymphocyte, Journal of Clinical Immunology, Sep. 2004, vol. 24, Issue 5, pp. 542-552, Gladson Muthian et al.
Curcumin Inhibits Experimental Allergic Encephalomyelitis by Blocking IL-12 Signaling Through Janus Kinase-STAT Pathway in T Lympocytes, The Journal of Immunology, pub. Jun. 15, 2002, vol. 168, No. 12 6506-6513, An Hu et al.
Resveratrol and curcumin enhance pancreatic B-cell function by inhibiting phosphoddiesterase activity, Journal of Endocrinology, Nov. 1, 2014 223 pp. 107-117, Michael Rouse et al.
Hespertin, a selective Phosphodiesterace 4 Inhibitor, Effectively Suppresses Ovalbumin-Induced Airway Hyperresponsiveness without Influencing Xylazine/Ketamine-Induced Anesthesia, Evidence-Based Complementary and Alternative Medicine, vol. 2012, Article ID 472897, 10 pages, Chung-Hung Shih et al.
Fatty acid-medicated inhibition of IL-12 production by murine macrophages is independent of PPAR (n-3 PUFA), British Journal of Nutrition, 2004, 91, pp. 733-739, Meijuan Zhang et al.
Regulation of interleukin-2 singnaling by fatty acids in human lympocytes (DHA), Journal of Lipid Research, Sep. 2007, vol. 48, pp. 2009-2019, Renata Gorjao et al.
Inhibitory effect of nicotinamide on in vitro and in vivo production of tumor necrosis factor-alpha, Immuno Lett Oct. 1997, 59 (1) pp. 7-11, Fukuzawa M. et al.
Eicosapentaenoic Acid and Docosahexaenoic Acid Reduce UVB and TNF-a-induced IL-8 Secretion in Keratinocytes and UVB-induced IL-8 in Fibroblasts (DHA), Journal of Investigative Dermatology, 920050, 124, pp. 248-255, Amy Storey et al.
Interaction of Dietary Fatty Acids with Tumour Necrosis Factor Family Cytokines during Colon Inflammation and Cancer (DHA, n3 PUFA), Mediation of Inflammation vol. 2014, Article ID 848632, 17 pages, Jirina Hofmanova et al.
Dietary polyunsaturated fatty acids and inflammatory mediator production (EPA, DHA), The American Journal of Clinical Nutrition, Am J Clin Nutr 200, 71 pp. 343S-348S, Michael J James et al.
Small Molecules: An Overview of Emerging Therapeutic Options in the Treatment of Psoriasis, Skin Therapy Letter, vol. 18, No. 7, Nov.-Dec. 2013, Melinda Gooderham, M.D.
Expanding research in Intracellular Signalling: Promising Data in Rheumatoid Arthritis with Small-Molecule Inhibitors, Mednet, Medical Frontiers—12th Annual European Congress of Rheumatology (EULAR), London, UK, May 25-28, 2011 3 pp, Dr.Lena Coic, Editor.
The Safety of Biologic Agents in the Treament of Inflammatory Bowel Disease, Minnesota Medicine, Jun. 2008, Chris Shepela, M.D.
Biological drug defined, NCI Dictionary of Cancer Terms.
TNF Alpha Inhibitors vs. Biologic Therapies in Crohn's disease, Healthline Published Mar. 2, 2012, Stephanie Faris.
Biochemical Significance of Proinflammatory Cytokines in Psoriasis vulgaris among Egyptian Patients, New York Science Journal 2010; 3 (10) pp. 58-66, Halla M. Ragab et al.

* cited by examiner

*Primary Examiner* — Layla Berry
(74) *Attorney, Agent, or Firm* — Ronald A. Sandler

(57) ABSTRACT

A method and composition for treating chronic inflammatory disorders comprising a pharmaceutically acceptable carrier suitable for oral administration or injection and containing a therapeutic amount of a complex of dietary supplement ingredients comprising nicotinamide, quercetin, curcumin, EPA, DHA, hesperetin and glychrrhizin.

7 Claims, No Drawings

METHOD AND COMPOSITIONS FOR TREATING CHRONIC INFLAMMATORY DISORDERS

TECHNICAL FIELD

The present invention relates to an immune-modulating dietary supplement for treating chronic disorders, such as psoriasis, rheumatoid arthritis, inflammatory bowel disease and uveitis.

BACKGROUND OF THE INVENTION

Inflammation is part of the body's attempt at self-protection, and functions to remove harmful stimuli and begin the healing process. Inflammatory disorders arise when inflammation becomes uncontrolled and causes destruction of healthy tissue. Inflammation can be acute or chronic. Acute inflammation has a rapid onset, often becomes severe, and usually resolves in days or weeks. Chronic inflammation generally progresses less rapidly, and may last for months or even years.

Although limited, mild to moderate psoriatic skin disease can often be controlled by topical agents; more severe disease usually requires systemic therapy. While psoriasis was once thought to be a local hyper-proliferative disorder of keratinocytes, it is now recognized that psoriasis is a chronic systemic inflammatory disease with a prominent role for the immune system. Psoriasis affects 2-3% of the U.S. population and is a source of substantial morbidity. Psoriasis often has a significant effect on patients' quality of life due both to the physical appearance of the skin lesions and the psychosocial consequence of their appearance.

Rheumatoid arthritis is the most common form of immune-mediated arthritis, affecting more than 1.3 million Americans, and is the most disabling type of arthritis. It most commonly affects the wrist and small joints of the hand. Inflammatory bowel disease (IBD) involves chronic inflammation of all or part of the lower digestive tract. The two most common types of IBD are ulcerative colitis and Crohn's disease. In Crohn's disease, inflammation can affect the entire digestive tract, while in ulcerative colitis, only the large intestine is affected by inflammation. Uveitis is a destructive inflammatory disease of the middle layer of the eye, and is the third leading cause of blindness worldwide. Uveitis can occur as an autoimmune disorder or as a result of injury, infection or exposure to toxins.

The recognition of the immune mediation of these disorders has led to a number of new therapeutic targets for these disorders. Among the principal targets are actions of proinflammatory cytokines and their associated transduction pathways, which include tumor necrosis factor alpha (TNF-α), various interleukins (especially IL-6 and IL-12), the Janus kinases (JAKS) and phosodiesterase-4 (PDE4). A number of recent studies suggest that the release of these cytokines and their transduction pathways contribute to the initiation or persistence of the inflammatory process in psoriasis, rheumatoid arthritis, IBD and uveitis.

The past 20 years have witnessed the development of a succession of biologic therapies for psoriasis, rheumatoid arthritis, inflammatory bowel disease and uveitis. Biologic therapies or biologicals are medicinal substances that are extracted from or synthesized from a living organism or its products for prevention or treatment of a disease. They interfere with specific components of the body's immune system and are consequently more targeted than older systemic treatments for many inflammatory disorders. Biologicals have proven to be effective therapies for these complex inflammatory diseases. However, while useful treatment options, biologicals have a number of limitations, including uncommon but extremely serious side effects (such as reduced ability to fight infections and a measurable increase in the incidence of lymphoma), high patient costs, and a lack of or loss of efficacy in a material number of patients.

These issues have prompted a continuing search for additional or alternative therapies which are directed at the inflammatory pathways. To improve patient response rates and reduce the substantial annual cost a patient and the U.S. health system is burdened with, I have investigated the therapeutic use of combinations of natural dietary constituents, a number of which have purported anti-inflammatory properties. I have discovered that a handful of natural dietary constituents combined in natural complexes, in very specific proportions, have clinically useful anti-inflammatory properties. Such complexes can be administered by themselves in pharmaceutical preparations designed for oral administration, e.g. tablets, capsules, oral solutions and suspensions for amelioration of psoriasis, rheumatoid arthritis, IBD and uveitis; or they can be administered in oral pharmaceutical preparations with other dietary supplement ingredients. Additionally, and perhaps most importantly, such complexes can be adjunctively administered with biologicals to improve patient responsiveness as well as potentially dramatically reduce costs of therapy.

SUMMARY OF THE INVENTION

The present invention relates to a method and composition for treating chronic inflammatory disorders, such as psoriasis, rheumatoid arthritis, inflammatory bowel disease and uveitis, administered orally or by intravenous or subcutaneous injection.

A principal object of the present invention is to provide a method and composition for treating chronic inflammatory conditions such as psoriasis, rheumatoid arthritis, inflammatory bowel disease and uveitis, comprising administering to patients with such inflammatory disorders a complex of natural dietary supplement ingredients in specific proportions, either providing the complex by itself or in combination with one or more biological agents.

Another object of the present invention is to provide a method of the type set forth wherein the complex of natural dietary supplement ingredients contains nicotinamide (aka niacinamide), curcumin, quercetin, hesperetin, eicosapentaenoic acid (EPA), docosahexaenoic acid (DHA) and glycyrrhizin.

A further object of the present invention is to provide a method of administering the natural dietary supplement ingredient complex as an adjunctive treatment for patients already receiving a biological agent for their condition in order to effect a greater improvement in their condition than with the biological alone.

Still another object of the present invention is to provide a composition for reducing inflammation in chronic inflammatory disorders comprising an amount of a small number of natural dietary supplement ingredients in proprietary proportions so that when such a composition is added to the biological drug in a patient's treatment regimen, the dosage of the biological can be reduced without adversely affecting the disease-state of the patient.

These and other objects of the present invention will be more readily understood when considered in conjunction with the following detailed description and examples.

DESCRIPTION OF THE PREFERRED EMBODIMENTS

In the practice of the invention, pharmaceutical preparations suitable for oral administration, including tablets, capsules, caplets and liquid solutions or suspensions are prepared containing a mixture nicotinamide, curcumin, quercetin, hesperetin, glycyrrhizin, EPA and DHA, and administered to patients with chronic inflammatory disorders experiencing exacerbations of their diseases. The complex/mixture contains these ingredients in the following concentrations by weight:

TABLE 1

| Ingredient | % By Weight in Oral Dosage Form |
|---|---|
| Nicotinamide | 20-40 |
| Quercetin | 10-15 |
| Curcumin | 10-20 |
| EPA | 12-26 |
| DHA | 4-12 |
| Hesperetin | 0.4-1 |
| Glycyrrhizin | 1-4 |

In addition to the percentage concentrations by weight listed in Table 1 for the seven ingredients constituting the natural dietary supplement immune-modulating complex, in order for unequivocal efficacy of the complex certain specific ratios of the ingredients must be present: 1) the ratio of EPA to DHA (EPA/DHA) must be $\geq 2.5 \leq 3.2$) the ratio of nicotinamide to quercetin+curcumin (N/Q&C) must be $\geq 0.80 \leq 1.50$.

In the practice of the invention, patients are administered by mouth or by intravenous or subcutaneous injection of the natural dietary supplement complex (the "Supplement Complex") in daily dosages of 400 mg to 4000 mg once daily or in divided doses administered 2 to 4 times per day. Oral dosages are incorporated into pharmaceutically acceptable dosage forms including tablets, capsules, caplets, and oral solutions or suspensions. Dosages provided for injection are incorporated into pharmaceutically acceptable solutions or stable suspensions.

The Supplement Complex may be administered by itself or in combination with other dietary supplement ingredients including, but not limited to, folic acid, vitamin A, vitamin D, vitamin C, vitamin E, thiamine, pyridoxine, riboflavin, pantothenic acid and biotin.

The Supplement Complex may be given as monotherapy or more commonly as adjunctive therapy with biologicals to patients with chronic inflammatory disorders. The following examples illustrate the present invention.

Example 1

A capsule containing 500 mg of a Supplement Complex containing 200 mg nicotinamide, 75 mg quercetin, 75 mg curcumin, 100 mg EPA, 40 mg DHA, 5 mg hesperetin and 5 mg glycyrrhizin was administered for 8 weeks to a 70 year old female with rheumatoid arthritis and moderate pain. After 4 weeks of receiving the dietary supplement, the patient reported mild joint pain and after 8 weeks of receiving the dietary supplement, she reported no joint pain.

Example 2

A 69 year old woman with a 40 plus year history of Crohn's disease ("CD") and multiple surgical procedures for CD, currently receiving 80 mg of Humira every other week and still experiencing frequent bloody stools and moderate pain, ingested for 4 weeks two capsules BID of a dietary supplement containing 811.6 mg complex comprised of 250 mg nicotinamide, 300 mg of a mixture of about 72% EPA and about 28% DHA, 100 mg quercetin, 133.3 mg curcumin, 23 mg glycyrrhizin, and 5.3 mg hesperetin. At the end of the 4-week period, she had less frequent stools and a reduction in pain.

Example 3

Nineteen (19) patients with moderate to severe plaque psoriasis, who were being treated with a biological agent (8 on Ustekinumab, 1 on Ustekinumab and Apremilast, 7 on Adalimumab, 3 on Etanercept), had a dietary supplement having the composition of Example 2 added to their treatment regimen. Each patient received 2 capsules of the dietary supplement once or twice daily for 8 weeks. Determination of clinical benefits were assessed by a Self-Administered Psoriasis Area Severity Index (SAPASI), a patient global rating of overall improvement and a rating of body surface area involvement. Of 11 patients with SAPASI>10 at baseline, 91% had an 8-week PASI 50 (50% improvement at 8 weeks). Sixty-three percent (63%) were rated by patients as Much Better or Better, and mean psoriasis surface area decreased by a mean of 35% by the end of the study.

Example 4

Nineteen (19) patients with untreated plaque psoriasis involving >5% body surface area were treated with the dietary supplement capsules as in Example 2 and 3 for 28 days. None of the patients had received any biological drug within 12 months or any other oral treatment for psoriasis within 3 months of entering the study. Serum biomarkers of inflammatory cytokines strongly associated with the pathogenesis of psoriasis (tumor Necrosis Factor-α, interleukin-2, interleukin-6 and interleukin-12) were measured at baseline and after the 28-day treatment period. Serum levels of IL-2 were below the level of quantification for all patients. By day 28, patients had an 18.6% decrease in serum TNF-α levels, and 53% had a mean decrease in IL6/IL12 serum levels of 47.3%.

It will be apparent to those skilled in the art that only the preferred embodiments have been described by way of exemplification, and that there are various modifications which fall within the scope of this invention.

What is claimed is:

1. A method of treating chronic inflammatory disorders in humans in need of such treatment comprising administering an immune-modulating dietary supplement complex containing a therapeutically effective amount of nicotinamide, quercetin, curcumin, EPA, DHA, hesperetin and glycyrrhizin.

2. The method of claim 1, wherein the dietary supplement ingredients are present in percentage ranges shown in the table below

| Ingredient | % By Weight in Oral Dosage Form |
|---|---|
| Nicotinamide | 20-40 |
| Quercetin | 10-15 |
| Curcumin | 10-20 |

-continued

| Ingredient | % By Weight in Oral Dosage Form |
|---|---|
| EPA | 12-26 |
| DHA | 4-12 |
| Hesperetin | 0.4-1 |
| Glycyrrhizin | 1-4. |

3. The method of claim 1, wherein the daily dosage of the dietary supplement complex is from about 400 mg to about 4000 mg.

4. The method of claim 1, wherein the daily dosage of the dietary supplement complex of about 400 mg to about 4000 mg is administered once daily or in divided doses administered 2 to 4 times per day.

5. The method of claim 1, wherein the ratio of EPA to DHA (EPA/DHA) must be ≥2.5 and ≤3.2 and the ratio of nicotinamide to the combination of quercetin and curcumin must be ≥0.80 and ≤1.50.

6. The method of claim 1, wherein the pharmaceutically acceptable carrier includes tablets, capsules, caplets, and solutions or suspensions, suitable for oral ingestion.

7. The method of claim 1, wherein the pharmaceutically acceptable carrier includes sterile solutions or suspensions suitable for intravenous or subcutaneous injection.

* * * * *